United States Patent [19]
Gilliksen

[11] Patent Number: 4,812,126
[45] Date of Patent: Mar. 14, 1989

[54] EDUCATION OR LEARNING AID METHOD

[76] Inventor: Byron Gilliksen, 6001 Idylwood Dr., Edina, Minn. 55436

[21] Appl. No.: 6,272

[22] Filed: Jan. 21, 1987

Related U.S. Application Data

[63] Continuation-in-part of Ser. No. 737,794, May 28, 1985, abandoned.

[51] Int. Cl.⁴ .................................................. A61B 5/05
[52] U.S. Cl. .................................... 434/238; 273/1 E; 273/DIG. 28; 128/734; 128/905
[58] Field of Search ................. 273/1 GC, 1 E, 85 G, 273/86 R, 86 A, DIG. 28; 434/233, 118, 236, 238; 128/630, 635, 640, 733, 734, 905

[56] References Cited

U.S. PATENT DOCUMENTS

| | | | |
|---|---|---|---|
| 3,996,671 | 12/1976 | Foster | 434/307 |
| 4,008,714 | 2/1977 | Silva et al. | 128/734 |
| 4,149,716 | 4/1979 | Scudder | 273/1 GC |
| 4,300,574 | 11/1981 | Briggs | 128/734 |
| 4,308,017 | 12/1981 | Laughon | 434/169 |
| 4,331,160 | 5/1982 | Zito, Sr. | 128/734 |
| 4,358,273 | 11/1982 | Yamamoto | 434/201 |
| 4,459,995 | 7/1984 | Conners et al. | 128/734 |
| 4,461,301 | 7/1984 | Ochs | 128/734 |
| 4,494,554 | 1/1985 | Van Dyke et al. | 128/734 |
| 4,557,271 | 12/1985 | Stoller et al. | 128/734 |

*Primary Examiner*—Maryann Lastova
*Attorney, Agent, or Firm*—Steven E. Kahm

[57] ABSTRACT

A new method of learning by use of a machine which interacts with the user to guide the user through a programmed series of questions. The system is based on finding trouble spots in the users logic or feelings by observing the users skin response to questions. The computer will ask the user a question. The machine measures the users skin resistance in response to the question and displays the response to the user. The user enters a response to the question on the computer keyboard based on the response he observes in his skin resistance which tells him how he is reacting to the question. The computer selects the next question based on his answer to the previous question and thus guides the user through a programmed series of questions. If troubled areas are uncovered the computer jumps to subroutines to help with that problem before moving on to the next step in the programmed series of questions.

4 Claims, 3 Drawing Sheets

EDUCATION OR LEARNING AID METHOD

BACKGROUND OF THE INVENTION

This invention relates to an education and teaching or learning aid and method used in conjunction with a personal computer and a CRT.

In the past there have been many learning aids developed using a device to pose a problem or question, a means of answering the question and a means of displaying the questions and answers. These learning aids typically pose a question and give immediate positive reinforcement for a correct answer or inform the user that the answer was incorrect and encourage or ask him to try again. The device will pose a series of questions and the user is programmed to remember the correct answers in hopes that he will remember the correct responses in the future. However these devices do not help the user isolate troubling thoughts or ideas or identify problems in the user's logic or thought process so that those trouble spots may be dealt with and cleared up such that the user can be guided in his conceptional understanding in addition to rote learning as the other devices previously introduced do.

BRIEF SUMMARY OF THE INVENTION

This invention employs a device to detect changes in the electrical resistance in the skin of the user, a means of converting the analog data so collected to a digital representation and special software to convert the digital data into a graphic representation on a CRT. The software is run on a personal computer to create the graphics. The software can also be used to print text on the CRT. The text can be used to direct the user's thoughts by focusing his attention on a question, idea or feeling. The computer's keyboard can be used to answer questions, or run the software.

The user's skin resistance responds to the thought directing text or questions posed and the user observes the graphic representation of the changes in the resistance of his skin.

There is a relationship between the observed changes in electrical resistance of the user's skin and his mental condition. Using this method the user can uncover areas of confusion, fear, anger, hate or other strong emotions by observing his reaction to the thought directing text or questions.

This is useful in uncovering blocks in logic which show up as confusion and are associated with a drop in the resistance in the skin. If the confusion points can be isolated the confusion may be cleared up by employing additional explanation at that point before continuing on in a programmed learning series of questions.

The method of using the invention is to focus the users attention on an idea, concept or feeling by having the computer ask the user a question. The user observes the change in his skins resistance in response to the question and selects a response to the question based on that change which he enters into the computer. The computer is programmed to ask the next question based on the answer to the previous question, thus guiding the user through a programmed series of learning exercises designed to help the user overcome any problems he might have in learning the subject area dealt with.

A BRIEF DESCRIPTION OF THE DRAWINGS

DETAILED DESCRIPTION OF THE INVENTION

Figure 1:
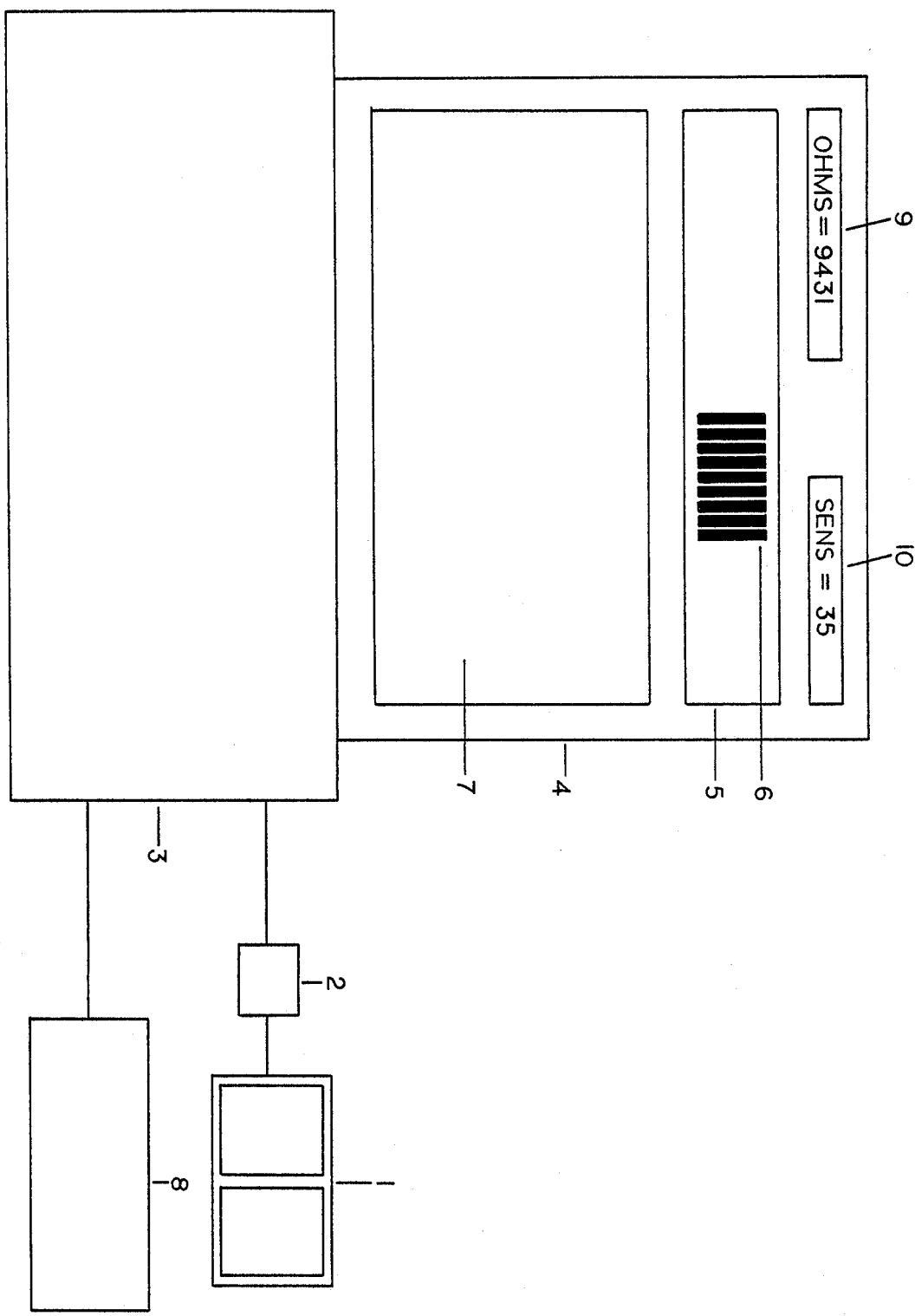
FIG. 1 shows the components of the invention.

FIG. 1, shows the component parts of the invention. It is composed of two electrodes, 1, which are preferably two copper plates set side by side. The hand of the user is placed on the plates so as to touch both at the same time, thus completing a bridge circuit, shown later in FIG. 2, with the hand of the user acting as one of the resistors.

The resistance measured at, 1, is part of a bridge circuit. The rest of the bridge circuit, plus a noise filter, an analog to digital converter, a register array, and an address and bus interface are all preferably located on card, 2. These components may be located anywhere but it is preferred to locate them all on a card which may be added to a computer. The card, 2, processes the resistance as measured at, 1, and changes the resistance measured to a digital current reading that the computer, 3, can use.

The computer, 3, is used to calculate the value of the resistance of the skin of the user from the digital current reading received from card, 2. The computer then converts the data to a graphic representation, 6, appearing in graphics window, 5, which is displayed on CRT, 4. In the preferred embodiment the graphics show a series of colored bars, 6, each bar representing a specific number of ohms.

The computer also displays the present resistance reading in ohms, 9, and the sensitivity setting, 10, on the CRT, 4. It is preferred that the questions or thought directing instructions asked of the user be printed as text, 7, on the CRT, 4, but any means of asking questions or directing the thoughts of the user is acceptable.

The computer keyboard, 8, can be used to respond to the questions posed, to set the sensitivity setting and to start, stop or control the software.

It is preferred to have a color CRT, 4, but any CRT will do so long as at least two distinct shadings of bars, 6, can be displayed. Using different colors makes it very easy for the user to distinguish at a glance if there is an increase or decrease in resistance and the number of bars displayed indicates the magnitude of the change.

It is preferred to have the text, 7, for the thought directing instructions or questions displayed just below the graphics window, 5, so that the user only has to shift his eyes up slightly to see the graph of the measured response to the question or thought directing instruction.

It is also preferred to have the questions or thought directing instructions asked on the CRT, 4, so that the software which controls the series of questions or thought directing instructions displayed can jump to subroutines to clear up troubled areas when required.

Figure 2:
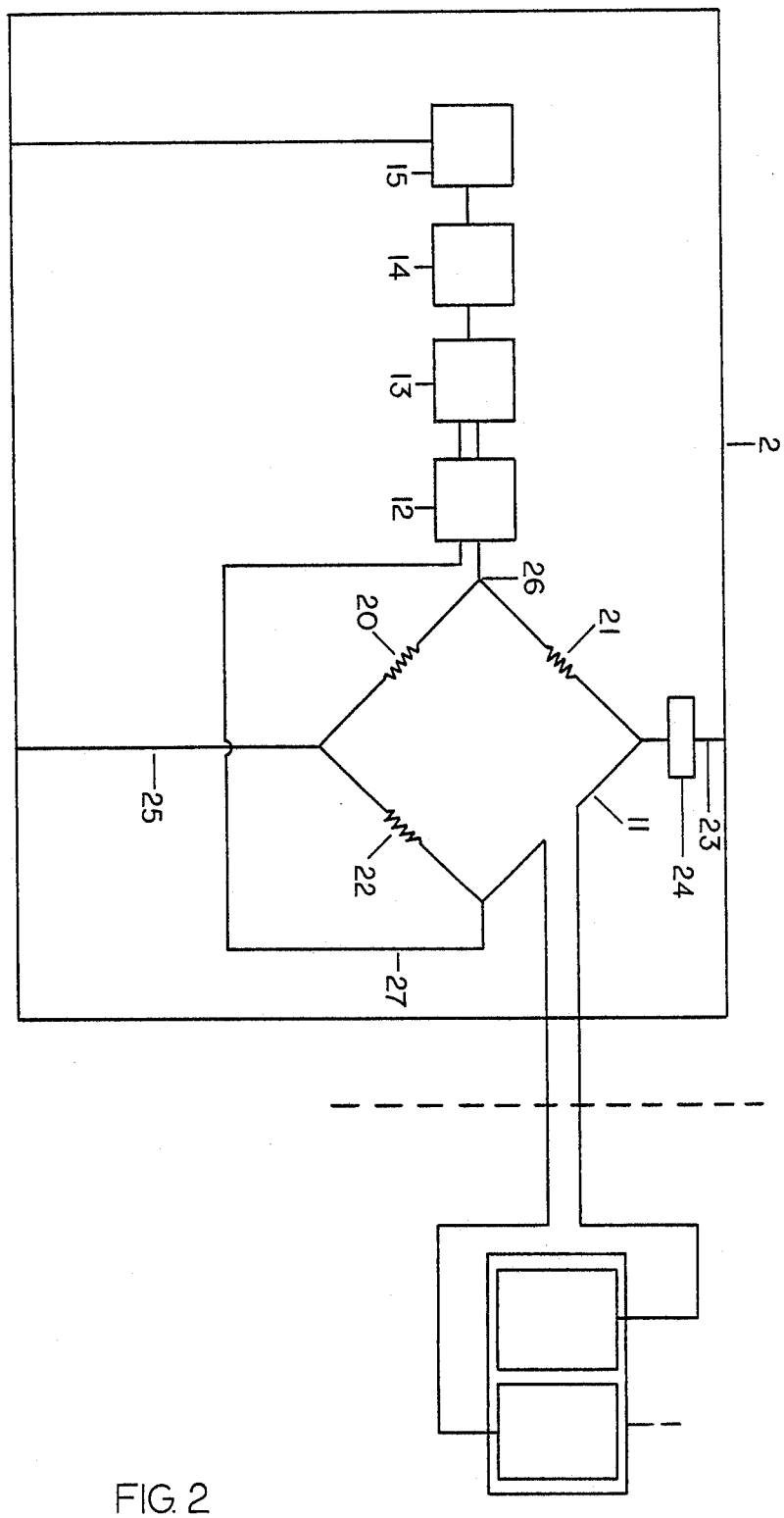
FIG. 2 shows a card containing a bridge circuit used to compare the resistance in the user's skin to a selected resistance in the hardware, an analog to digital conversion chip, a noise filter, a register array, an address code and bus interface, and a fuse.

FIG. 2 shows a card, 2, containing a bridge circuit, 11, a noise filter, 12, an analog to digital converter, 13, a register array, 14, an address code and bus interface, 15, and a fuse, 24.

The bridge consists of two resistors of the same value, 20 and 21, a 9,000 ohm resistor, 22, (all on the card, 2) and the skin of the user, acting as a resistor between the two electrodes, 1, is the fourth resistor. The bridge circuit is powered, in this embodiment by a five volt D.C. source, 23, from the computer, 3. There is a fuse, 24, to protect the system, and a ground, 25.

Thus the resistance of the skin is compared to a 9,000 ohm resistor.

When the device is operating and a person places his hand on electrodes 1, completing the bridge circuit, measurements are made comparing the resistance in the skin of the hand of the user, 1, to a 9,000 ohm resister, 22. When the bridge is balanced the skin of the user is producing a 9,000 ohm resistance and there is no current leaving the bridge between 26 and 27. When the skin's resistance as measured at 1, is less than 9,000 ohms the bridge is unbalanced and a negative current is measured between 26 and 27. When the skin's resistance is greater than 9,000 ohms a positive current is measured between 26 and 27.

To obtain better results the analog data collected from the bridge circuit at points 26 and 27, is processed by a noise reduction filter, 12. The resultant analog signal is converted to a digital signal, by an analog to digital converter, 13, so the computer, 3, can process the data in digital form.

The digital data is then stored in an 8×8 register array, 14, and sent to the address code and bus interface, 15, were the data is coded for use in the computer, 3.

Figure 3:
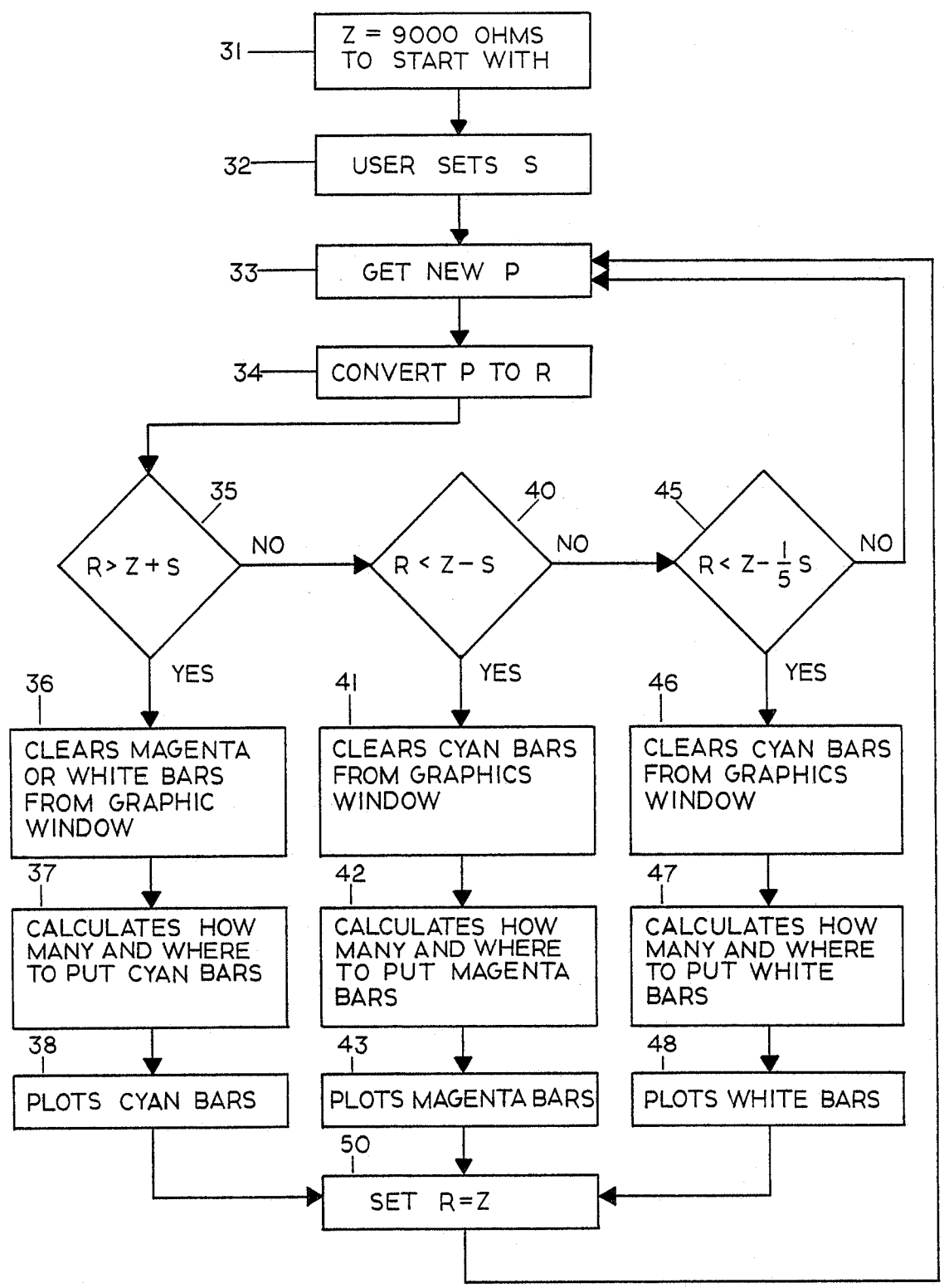
FIG. 3 shows a chart of the logic used to create the graphics.

FIG. 3 shows a flowchart of the software used to create the graphics in the preferred embodiment of the invention. The preferred embodiment uses a color CRT. There are two preferred methods of creating the bar graphs.

In the first method two colors, cyan and magenta are used. The cyan bars are plotted in the graphics window for increases in resistance and magenta bars are plotted for decreases in resistance.

In the second method three colors, cyan, magenta and white are used. Since it is more important to track the decreases in resistance it is useful to have a means of following the decreases in the resistance more accurately than the increases. This can be accomplished by using a third color, white, to show decreases in resistance too small to show up in the first method. This can be done by setting the white bars equal to one fifth the value of the cyan bars.

In the preferred embodiment the software will allow the user to choose which method to use.

Referring to FIG. 3, and using method one, starting at block 31, the program sets an initial value for, Z, the last used resistance measured through the skin of the user at 9,000 ohms.

At block 32, the user is allowed to set the sensitivity, S, which will be the value in ohms of each magenta or cyan bar used in the graphics.

At block 33, the program calls for the present value of the skins resistance as measured at 1, which is stored in, 15, in digital form. The reading in, 15, is a current, P, from the bridge and must be converted to an ohm reading, R, as is done in block 34, by use of the formula $R = ((100/(100((P \times 0.0005 + 2.5) \times 20))) \times 9,000) - 9,000$. This value of R is the present value of the resistance and is compared to the previous value of the resistance Z, which is set to 9,000 ohms to begin with.

Following the logic of blocks 35 to 50 (for method one blocks 45, 46, 47, and 48 are not used) the program now decides how many, what color, and where to place the bars, 6, in graphic window, 5. There are three cases to describe.

CASE 1

At block 35, the present resistance reading, R, is compared to, Z, the previous resistance reading plus the sensitivity setting, S. If $R > Z + S$ then the program proceeds to block 36 where it clears the graphics window, 5, if magenta bars are displayed. Block 37 calculates the number of bars to be placed on the graph, based on one bar for each multiple of the sensitivity. The number of bars plotted is $(R - Z)/S$ rounded to the nearest integer. The program then plots the number of cyan bars on the screen in the appropriate place, 38, sets a new value of Z equal to the R value just used, 50, and then loops back to, 33.

The place where the bars are plotted, in 37, follow these rules:

If the previous reading was positive i.e. $(R > Z + S)$, and this reading was positive, add the additional bars for the new total to the left of the previous graph.

If the previous reading was negative i.e. $(R < Z - S)$, clear the graphics window, 5, and start placing the bars from the right most bar of the previous reading, and move left.

If it is the first reading or if the new graph is about to run off the graphics window, 5, start from the middle and move left.

CASE 2

A new value of P in, 15, is called up to, 33, and converted to a value for R in, 34. If in, 35, the value of $R > Z + S$ the program proceeds to, 36, as before. If the value of R is not $> Z + S$ at, 35, then the program goes to 40. At, 40, the program tests to see if $R < Z - S$, if yes then the program goes to, 41, which clears the graphics window, 5, if there are cyan bars on it.

Block 42, then calculates the number of bars to be placed on the graph. The number of bars plotted is $(R - Z)/S$ rounded to the nearest integer. The program then plots the number of magenta bars on the graphics window, 5, in the appropriate place, 43, and 50, sets Z to the value of R just used and loops back to, 33.

The place were the bars are plotted in, 42, follow these rules;

If the previous reading was positive and this reading is negative place the first bar at the left most previous bar and then add bars to the right until the proper number of bars are plotted.

If the previous reading was negative then add the appropriate number of bars to the right of where the previous bars left off to make the new total.

If this is the first reading or if the reading is about to go off the graphics window, 5, then start from the middle and go to the right.

CASE 3

If the new reading for R at, 34, goes to, 35, and 40 and the answer is no in each case, then there is not enough of a change from the previous reading and the graph is not changed. The program then loops from, 40, to, 33, for the next reading.

The software calls for a new, P, to be called up from, 15, to, 32, an average of six times a second, depending on the number of bars which need to be plotted.

For method two, starting at block 31, the program sets an initial value for, Z, the last used resistance measured through the skin of the user, at 9,000 ohms.

At block 32, the user is allowed to set the sensitivity, S, which will be the value in ohms of each magenta or cyan bar used in the graphics. The white bars will be one fifth of the value of the sensitivity setting.

At block 33, the program calls for the present value of the skins resistance as measured at 1, which is stored in, 15, in digital form. The reading in, 15, is a current, P, from the bridge and must be converted to an ohm reading, R, as is done in block 34, by use of the formula $R=((100/(100((P\times 0.0005+2.5)>20)))\times 9,000)-9,000$. This value of R is the present value of the resistance and is compared to the previous value of the resistance Z, which is set to 9,000 ohms to begin with.

Following the logic of blocks 35 to 50 the program now decides how many, what color, and where to place the bars, 6, in graphic window, 5. There are four cases to describe.

CASE 1

At block 35, the present resistance reading, R, is compared to, Z, the previous resistance reading plus the sensitivity setting, S. If $R>Z+S$ then the program proceeds to block 36 where it clears the graphics window, 5, if magenta or white bars are displayed. Block 37 calculates the number of bars to be placed on the graph, based on one bar for each multiple of the sensitivity. The number of bars plotted is $(R-Z)/S$ rounded to the nearest integer. The program then plots the number of cyan bars on the screen in the appropriate place, 38, sets a new value of Z equal to the R value just used, 50, and then loops back to, 33.

The place where the bars are plotted, in 37, follow these rules;

If the previous reading was positive i.e. $(R>Z+S)$, and this reading was positive, add the additional bars for the new total to the left of the previous graph.

If the previous reading was negative i.e. $(R<Z-S$ or $R<Z-S/5)$, clear the graphics window, 5, and start placing the bars from the right most bar of the previous reading, and move left.

If it is the first reading or if the new graph is about to run off the graphics window, 5, start from the middle and move left.

CASE 2

A new value of P in, 15, is called up to, 33, and converted to a value for R in, 34. If in, 35, the value of $R>Z+S$ the program proceeds to, 36, as before. If the value of R is not $>Z+S$ at, 35, then the program goes to 40. At, 40, the program tests to see if $R<Z-S$, if yes then the program goes to, 41, which clears the graphics window, 5, if there are cyan bars on it.

Block 42, then calculates the number of bars to be placed on the graph. The number of bars plotted is $(R-Z)/S$ rounded to the nearest integer. The program then plots the number of magenta bars on the graphics window, 5, in the appropriate place, 43, and 50, sets Z to the value of R just used and loops back to, 33.

The place were the bars are plotted in, 42, follow these rules;

If the previous reading was positive and this reading is negative place the first bar at the left most previous bar and then add bars to the right until the proper number of bars are plotted.

If the previous reading was negative then add the appropriate number of bars to the right of where the previous bars left off to make the new total.

If this is the first reading or if the reading is about to go off the graphics window, 5, then start from the middle and go to the right.

CASE 3

If the new value of P in, 33, converted to R in, 34, is only slightly more negative than the previous reading (less than one sensitivity setting, S) then it will go from, 34, to, 35, to, 40, to, 45 where it will be tested to see if $R<Z-(S/5)$. If the difference is over 1/5 of S then the program goes to 46 where the graphics window, 5, is cleared of any cyan bars. The program then moves to block 47 which calculates how many white bars to plot by the following formula, $(R-Z)/(S/5)$ rounded to the nearest integer. The program then plots the proper number of white bars in the appropriate place in block 48, sets the value of Z to the last used value of R in block 50, and loops back to 33.

The place were the bars are plotted in 47 follows these rules;

If the previous reading was positive clear the graphics window, 5, and plot the appropriate number of white bars starting from the left most previous bar and go to the right. If the previous reading was negative place the proper number of white bars to the right of the magenta or white bars and move to the right.

If this is the first reading or if the graph is about to go off the graphics window, 5, then shift to the middle of the graphics window and add to the right.

CASE 4

If the new reading for R at, 34, goes to, 35, 40, and 45 and the answer is no in each case, then there is not enough of a change from the previous reading and the graph is not changed. The program then loops from, 45, to, 33, for the next reading.

The software calls for a new, P, to be called up from, 15, to, 32, an average of six times a second, depending on the number of bars which need to be plotted.

For both methods one and two the software allows the user to select the sensitivity setting and change it at any time. Changing the sensitivity setting will change the number of bars, 6, plotted in the graphics window, 5. The software converts the digital current reading to ohms and then plots a series of colored bars corresponding to the changes in the resistance from the previous reading.

For methods one and two, if the reading is positive compared to the previous reading then the graph shows cyan bars moving to the left. If the reading is negative compared to the previous reading then the graph shows magenta bars moving to the right.

For method two, if the change is negative but only by an amount less than the sensitivity set on the program then white bars are added to the right of the magenta bars to show the decrease in the resistance.

If there was no change in the resistance reading then there is no change on the graph. The colors are not important so long as the plus and minus readings can be easily distinguished. Using the graph the user can easily observe the changes occurring and use this information in conjunction with the learning process herein disclosed.

There is an observable relationship between the electrical resistance as measured in the skin and the mental state of the user. When the user is in a mental state showing confusion, non understanding, hate, fear or other strong negative emotions the resistance measured in the skin of the user will drop. This will show up as a right movement of bars on the graphic display, 5. When the user observes a flowing motion in the graphics it indicates a continuous change in resistance either positive or negative which indicates an understanding, high interest, enthusiasm, a high emotional level, absence of difficulty, or good feelings in response to focusing his attention on the thought, idea, feeling or concept as instructed.

No change in the graphics indicates no change in resistance and has no meaning. Left movements in the graphics indicate increasing resistance and likewise has no meaning.

With the knowledge of the significance of the graphics, once the user has logged some time on the invention, he can use the invention to isolate troubling ideas or concepts in a programmed learning series of questions and zero in on the troubling concept or ideas so as to enhance the learning process by catching and removing troubled areas before moving on to the next step in the series of questions.

The software preferably has subroutines associated with certain questions that are common problem areas, for additional explanation of certain points. This is designed to clear up problems, before returning to the main programmed series of questions.

The invention is also useful in spotting concepts, feelings or attitudes in psychological evaluations, that the user may be repressing, so that the troubled areas may be identified and dealt with.

With the above in mind the method of use is to have the user place his hand on the copper electrodes, 1, so that the skin of his hand is the resistance being measured by the bridge circuit.

The user then reads the question posed to him on the screen and observes the graph of his skin resistance for changes in response to reading the question.

After observing the graph of the change in skin resistance, the user determines a response to the question, based on the observed change in skin resistance, which he enters into the computer by use of the computer keyboard.

The computer then selects the next question to be asked based on the response to the question just posed.

The above steps are now repeated as the user reads the new question, observes his skin resistance reaction to it by the graph on the screen, selects his response to the question based on the observed skin resistance change, etc. until the user quits or the programmed series of instructions in completed.

The computer can keep track of the answers to the questions for analysis, scoring or other uses.

There are many other possible applications for using the method of directing the user's thoughts to some feeling, idea, concept or question, and observing the resultant changes in resistance in the skin of the user to isolate troubling areas.

That which is claimed is:

1. An educational or learning aid method comprising:
a computer,
software for the computer,
a CRT,
two electrodes in contact with the skin of a user so that the skin of the user acts as a resistor between the two electrodes,
a bridge circuit with the skin of the user as the variable resistor which is to be measured,
a means of applying a potential difference across the bridge circuit,
a means of detecting the changes in the current flowing from the bridge circuit so as to measure the changes in resistance in the skin of the user,
a means of converting the measured changes in the resistance in the skin of the user to a cognitive representation,
a means of asking questions of the user,
a computer keyboard used in conjunction with the computer and software, for setting variables in the software, starting the program, and answering questions posed if called for,
where the user is asked a question,
the bridge circuit measures the change in the user's skin resistance in response to the question and presents a cognitive representation of the change in skin resistance to the user,
the user selects a response to the question based on the observed change in his skin resistance and enters this response to the computer by use of the computer keyboard,
the computer then selects the next question to be posed to the user based on his response to the previous question in a programmed series of questions.

2. An educational or learning aid method as in claim 1 where the cognitive representation of of the skins resistance is a visual graphic display on the CRT, the user observes the graphic display on the CRT and then selects a response to the question.

3. An educational or learning aid method comprising:
a computer,
software for the computer,
a CRT,
two electrodes composed of copper plates placed close together on an insulated board such that the hand of the user may be placed across both copper plates at the same time so that the skin of the user acts as a resistor between the two electrodes,
a bridge circuit with the skin of the user as the variable resistor which is to be measured,
a means of applying a potential difference across the bridge circuit,
the current flowing from the bridge circuit goes to a card containing a noise filter to improve the quality of the analog current data, an analog to digital converter to change the analog current data to digital current data, an $8 \times 8$ register array to store the digital data, and an address code and bus interface to code the data for use in the computer,
the computer, using the software, receives the digital data from the bus interface and converts it to a visual cognitive representation of the resistance, displayed on the CRT,
a means of asking questions of the user,
a computer keyboard used in conjunction with the computer and software, for setting variables in the software, starting the program, and answering questions posed if called for,
where the user is asked a question,
the bridge circuit measures the change in the user's skin resistance in response to the question and presents a cognitive representation of the change in skin resistance to the user,
the user selects a response to the question based on the observed change in his skin resistance and enters this response to the computer by use of the computer keyboard,
the computer then selects the next question to be posed to the user based on his response to the previous question in a programmed series of questions.

4. An educational or learning aid method as in claim 3 where the cognitive representation of of the skins resistance is a visual graphic display on the CRT, the user observes the graphic display on the CRT and then selects a response to the question.

* * * * *